Figure 3:
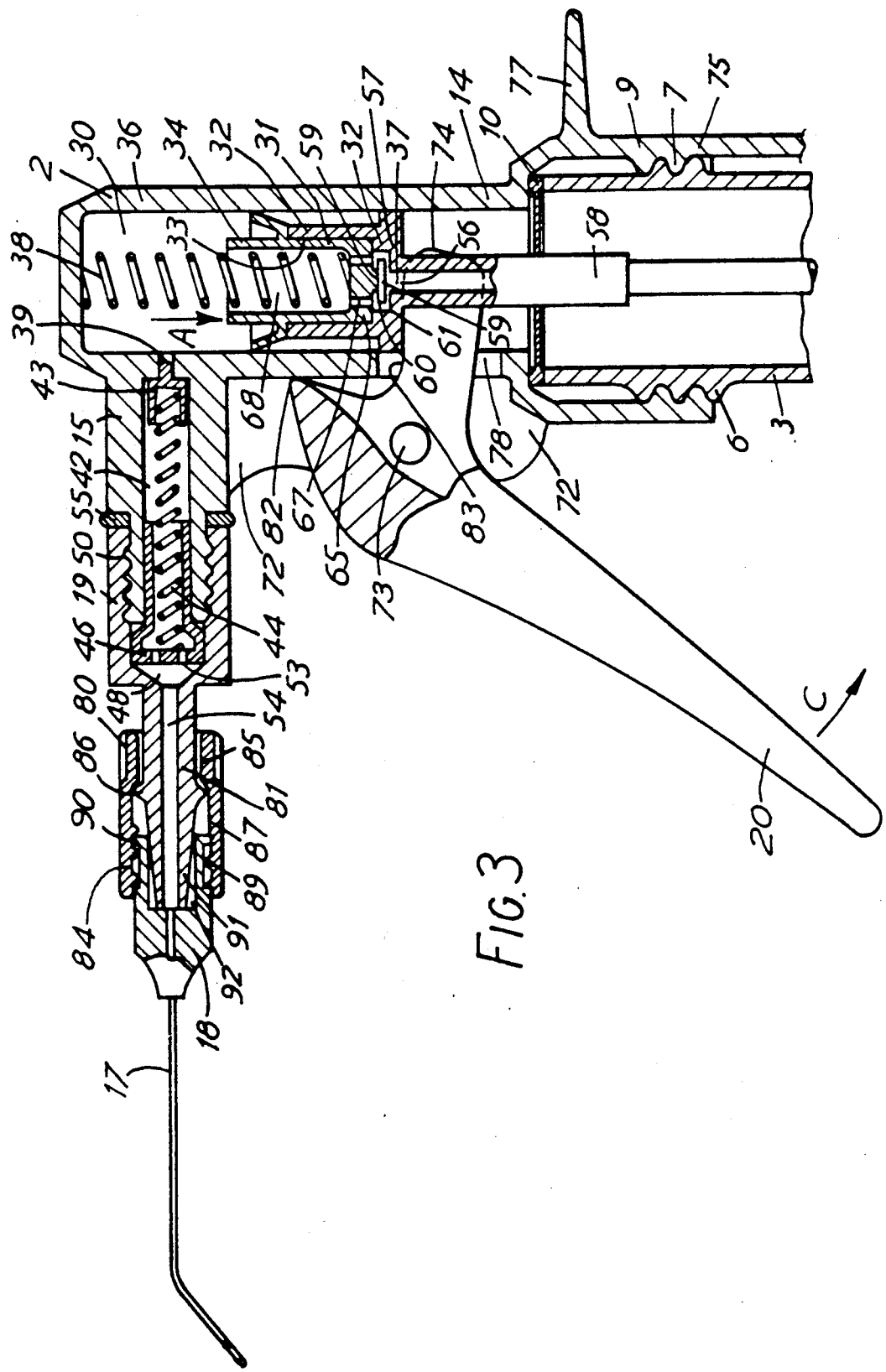

United States Patent [19]
Kandler et al.

[11] Patent Number: 5,033,961
[45] Date of Patent: Jul. 23, 1991

[54] FLUID DISPENSER

[75] Inventors: Harold J. Kandler, London, England; Phillip Robinson, County Galway, Ireland

[73] Assignee: Galway Dental Technology Limited, Dublin, Ireland

[21] Appl. No.: 448,108

[22] Filed: Dec. 13, 1989

[30] Foreign Application Priority Data

Dec. 14, 1988 [IE] Ireland ............................ 3722/88

[51] Int. Cl.$^5$ ............................................. A61C 5/04
[52] U.S. Cl. ........................................ 433/89; 433/80
[58] Field of Search ............................ 433/90, 89, 80; 604/187, 208, 247

[56] References Cited

U.S. PATENT DOCUMENTS

| | | | |
|---|---|---|---|
| 2,102,591 | 12/1937 | Hagemeier | 433/90 |
| 3,144,867 | 8/1964 | Trupp et al. | 433/88 |
| 3,164,153 | 1/1965 | Zorzi | 433/88 |
| 3,452,745 | 7/1969 | Hutchinson et al. | 128/66 |
| 3,480,009 | 11/1969 | Sinai | 128/66 |
| 4,276,880 | 7/1981 | Malmin | 433/80 |
| 4,406,881 | 9/1983 | Ladanyi | 424/49 |
| 4,861,339 | 8/1989 | Jonischkeit | 604/187 |

Primary Examiner—John J. Wilson
Attorney, Agent, or Firm—Browdy and Neimark

[57] ABSTRACT

A device for dispensing a treatment fluid (such as chlorhexidine) for the treatment of a dental disorder (such as periodontitis), the device (10) comprising a housing (14) for receiving a reservoir (3) for storing the treatment fluid, dispensing means (17,80-92) for dispensing treatment fluid to the area of the disorder and pump means (30-63) for metering and delivering a predetermined quantity of the fluid from the reservoir (3) to the dispensing means (17,80-92), wherein the dispensing means (17,80-92) comprises a cannula (17) removably connectable to the housing (14) and having an angled distal portion (21) for delivery of the treatment fluid to the area of the disorder, means (80-90) being provided for locating the cannula (17) selectively in two positions such that the distal portion (21) can be directed in two different directions, e.g. at substantially 180° to one another.

12 Claims, 4 Drawing Sheets

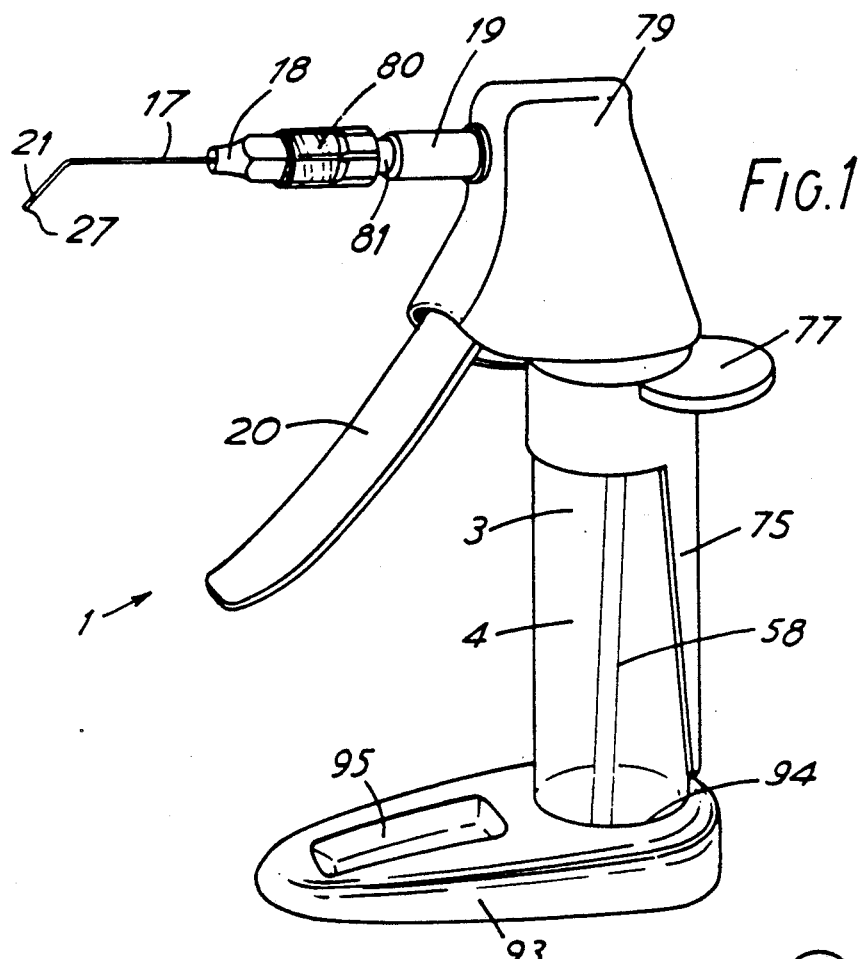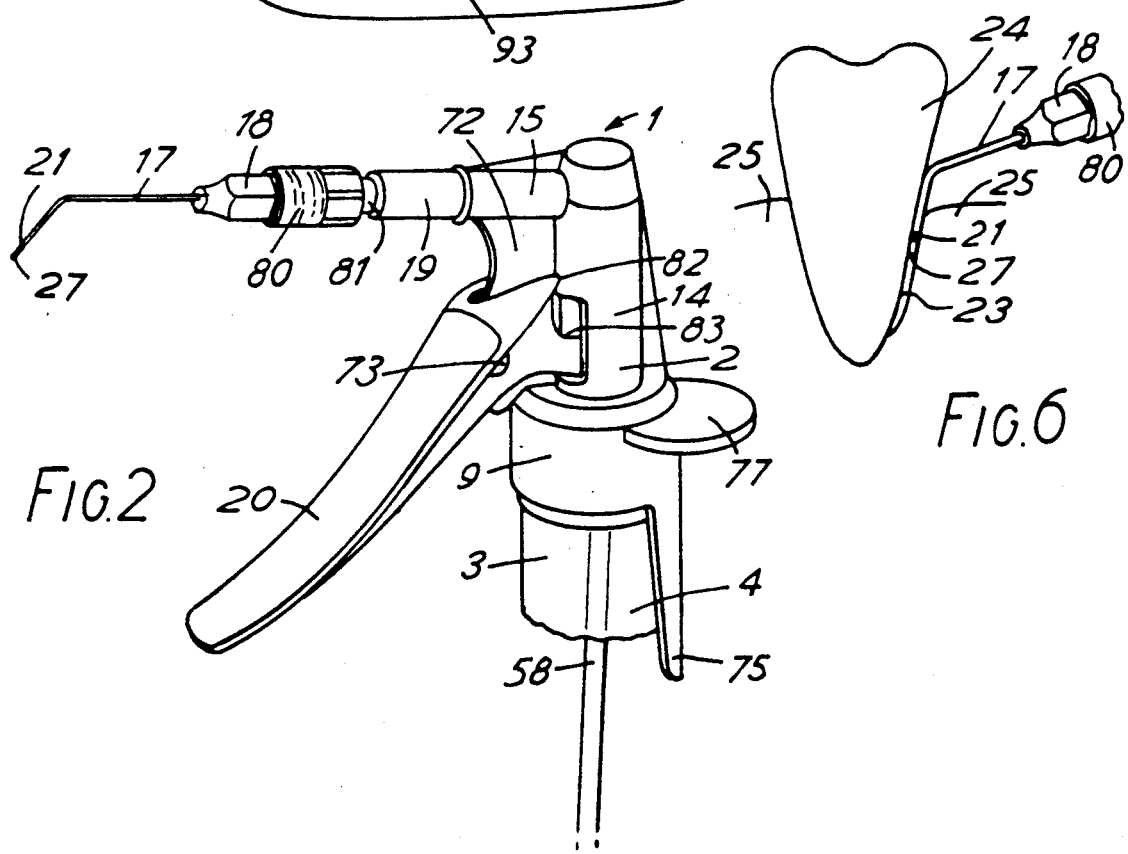

FLUID DISPENSER

The present invention relates to a device for dispensing fluid for the treatment of dental disorders, and in particular—though not limited to—to a device for dispensing fluid for the treatment of periodontitis.

Periodontitis is a disease which affects the gums of an individual. Bacteria caused by a build-up of plaque on the teeth attacks the gum and causes the gum to be detached from the tooth. As the gum begins to detach from the tooth a pocket is formed between the tooth and gum where further bacteria accumulates, thereby progressively worsening the condition. Chemical compositions, generally in liquid form, are provided for the local treatment of periodontitis. A typical composition is chlorhexidine, which is sold under a number of Trade Marks, some of which are ELUDRIL, CORSODYL, and PERIDEX.

To treat this condition and avoid gum trauma, it is important that relatively accurately measured predetermined quantities of the treatment composition are deposited directly in the diseased area, namely in the pocket between the gum and the tooth. The known apparatus for achieving this tends to be relatively complex and cumbersome and also relatively expensive. In general, existing apparatus is principally used in hospitals and dental surgeries. Attempts have been made to provide reasonably priced dispensing apparatus for dispensing a treatment composition which are usable by the patient at home, however, such attempts so far have failed.

In general, the only device available at an economical price for home use is a conventional syringe. A syringe, when used intra orally, requires considerable manual dexterity and it is not possible to dispense the treatment composition accurately in the diseased pocket. In general, periodontitis attacks a number of teeth simultaneously, and this thereofore requires refilling of the syringe after each tooth has been treated, otherwise, it would not be possible to maintain with any accuracy the quantity of treatment composition dispensed to each tooth. Because of the shape and construction of a syringe, it is relatively difficult (and in many cases impossible) to deposit the treatment composition precisely at the diseased pocket.

There is therefore a need for a device for dispensing a treatment fluid for treating a dental disorder, particularly, but not exclusively, for treating periodontitis.

According to this invention there is provided a device for dispensing a treatment fluid for the treatment of a dental disorder, the device comprising a housing for receiving a reservoir for storing the treatment fluid, dispensing means for dispensing treatment fluid to the area of the disorder and pump means for metering and delivering a predetermined quantity of the fluid from the reservoir to the dispensing means, wherein the dispensing means comprises a cannula having an angled distal portion for delivery of the treatment fluid to the area of the disorder, means being provided for locating the cannula selectively in two positions in which the distal portion is directed in two different directions (e.g. at 180° to one another for treatment of upper teeth and lower teeth).

Advantageously the cannula is removably connectable to the housing (e.g. by a Luer lock).

In one embodiment of the invention, the pump means is provided by a piston pump and preferably stop means are provided to limit the length of the piston stroke to a predetermined length. Preferably the piston pump is actuable by a trigger-like finger-operable lever that is pivotably mounted on the housing, said stop means being provided by engagement of the lever and the housing.

In another embodiment of the invention, non-return valve means are provided in an inlet to and in an outlet from a compression chamber of the pump. Preferably, an outlet from the compression chamber of the pump is provided in a side wall of the compression chamber.

In another embodiment of the invention, an inlet to the compression chamber is provided through the piston, the non-return valve means being provided in the inlet in the piston. Advantageously, a tube extends from the piston into the reservoir to draw fluid therefrom, the tube being movable with the piston.

In another embodiment of the invention, the housing comprises an elongated tubular portion forming the fluid reservoir and a hand grip for the device, a portion of the housing extending upwardly from the tubular housing to house the pump. Preferably, a finger operated lever is pivotally mounted on the housing for moving the piston in the piston pump, the lever being pivotal towards and away from the tubular portion of the housing. Advantageously, the lever is movable towards the housing to deliver fluid from the pump and is movable away from the housing to draw fluid into the piston pump. In one embodiment of the invention, the stop means are provided on the lever.

In another embodiment of the invention, the reservoir is releasably connected to the housing.

Preferably an outlet housing, having an outlet bore extending therethrough communicating with the outlet from the compression chamber of the piston pump, extends laterally away from the upper portion of the housing. Advantageously, the non-return valve means is mounted in the outlet housing.

Preferably, a web extends from the outlet housing to the upper portion of the housing to support pivotally the said lever. Advantageously, the outlet housing terminates in a tapered portion to be received in a correspondingly tapered socket of the dispensing means. Preferably, a ferrule is rotatably mounted on the end of the outlet housing to engage a receiver of a Luer lock of the socket.

In another embodiment of the invention, a dispensing means is provided, the dispensing means comprising a Luer lock socket and a cannula extending therefrom having an outlet at its distal end through the side wall of the cannula.

Advantageously, the device is suitable for the treatment of periodonitits.

Figure 4:
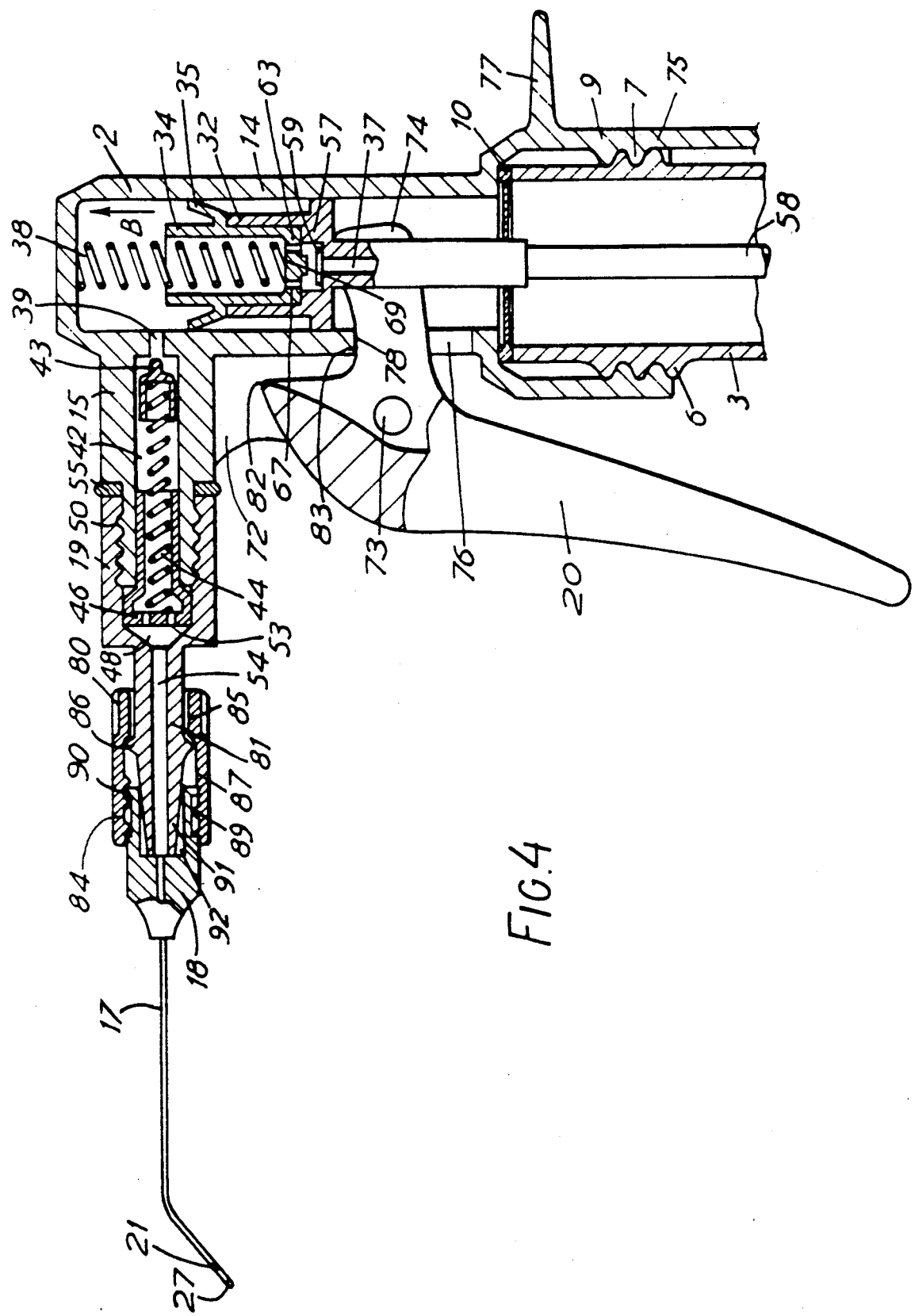
Figure 5:
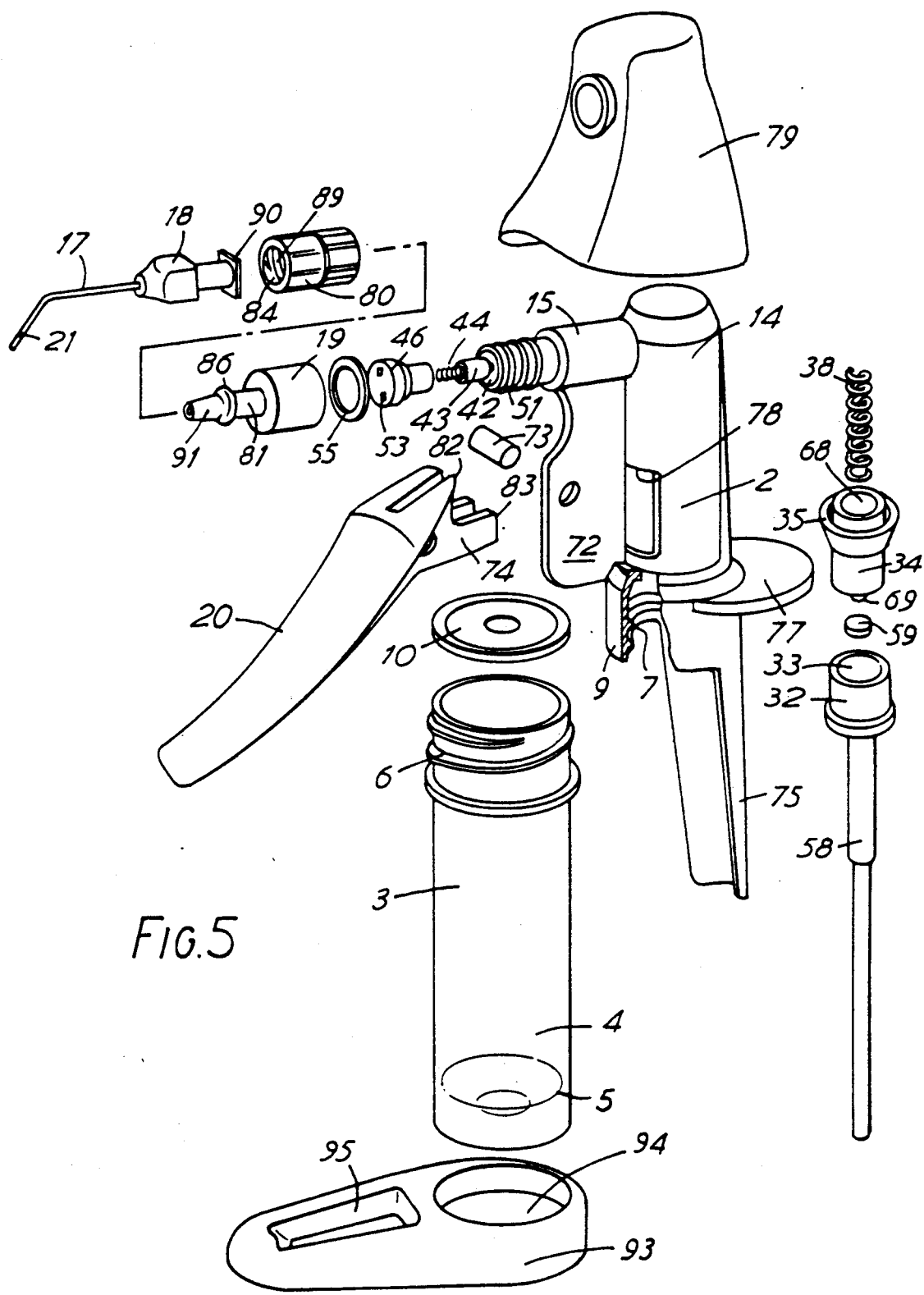

The invention will be more clearly understood from the following description of an embodiment thereof given, by way of example only, with reference to the accompanying drawings, in which:

FIG. 1 is a perspective view of a device according to the invention for dispensing treatment fluid for the treatment of a dental disorder, FIG. 2 is a perspective view of portion of the device of FIG. 1, FIG. 3 is a cross sectional view of portion of the device of FIG. 1 in one position, FIG. 4 is a cross sectional view similar to FIG. 2 of the device in a different position, FIG. 5 is an exploded perspective view of the device of FIG. 1, and FIG. 6 is a perspective view of a portion of the device in use.

FIGS. 1 to 5 illustrate a device 1 according to the present invention for dispensing a treatment fluid, in this case chlorhexidine for the treatment of periodontitis. The device 1 comprises a main housing 2 for receiving a reservoir 3. The reservoir 3 is formed by a tubular housing 4 closed by a lower end cap 5 and having threads 6 at its upper end to engage corresponding threads 7 in a cap portion 9 of the housing 2. The reservoir 3 may be filled from a stock bottle supplied by the chlorhexidine manufacturer or may be a smaller-sized tubular container which such manufactuers may supply. Thus, a full container of chlorhexidine may be screwed into the cap portion 9 to form the reservoir 3. A sealing ring 10 is provided in the cap portion 9 for sealing the joint between the cap portion 9 and the reservoir 3.

A pump means, in this case provided by a piston pump 11 described below, is formed in an upper portion 14 of the housing 2. An outlet portion 15 of the housing 2 receives a dispensing means comprising a cannula 17 extending from a Luer lock socket 18 that is releasably connected to a spigot cap 19 rotatably mounted on the outlet housing 15, as will be described below. The distal end portion of the cannula 17 is directed at an obtuse angle to the portion extending axially from socket 18. A lever 20 pivotally connected to the housing 2 operates the piston pump 11, as will be described below, for delivering a metered quantity of chlorhexidine from the reservoir 3 into the dispensing cannula 17. An outlet opening 21 to one side of the dispensing cannula adjacent the distal end 27 dispenses the fluid into a diseased pocket 23 formed between a tooth 24 and gum 25 as illustrated in FIG. 6 and described below. The distal end 27 of the cannula 17 is closed.

The piston pump 11 in the upper portion 14 of the housing 2 will now be described. The housing 14 forms a compression chamber 30 within which a piston 31 is slidable. The piston 31 comprises a main piston member 32 having a bore 33 within which is mounted a piston sealing member 34. A sealing ring 35 of flexible plastics material extends circumferentially around the sealing member 34 to engage sealingly the cylindrical side wall 36 of the compression chamber 30. A spring 38 biases the piston 31 in the direction of the arrow A. An inlet 37 to the compression chamber 30 is provided through the piston 31, as will be described below, and an outlet 39 through the side wall 36 renders the compression chamber 30 in communication with a bore 42 extending through the outlet housing 15. A non-return valve means comprises a plug 43 to engage sealingly the outlet 39 and thereby prevent fluid flowing back into the compression chamber 30 when the piston 31 is moving in the direction of the arrow A, see FIGS. 3 and 4.

The inlet 37 to the compression chamber 30 provided in the piston 31 is formed by an opening 56 in an end bight wall or cap 57 of the main piston member 32. A tube 58 extends downwardly from the end cap 57 into the reservoir 3 for drawing fluid from the reservoir. A non-return valve means, to prevent fluid returning to the reservoir from the compression chamber when the piston is being moved in the direction of the arrow B, is provided by a disc 59 which seals the outlet opening 56. The disc 59 is a loose fit in a chamber 60 formed by a bore 61 in the end cap 57 and closed by an end bight wall or cap 63 of the sealing member 34. A pair of ducts 67 through the end cap 63 deliver fluid from the chamber 60 into a bore 68 through the sealing member 34 into the compression chamber 30. A depending spud 69 extending from the end cap 63 of the sealing member 34 prevents the disc 59 sealing the ducts 67. However, as soon as the pressure of the fluid in the compression chamber 30 exceeds the pressure of the fluid in the reservoir 3, the disc 59 is biased by the fluid pressure into engagement with the end cap 57 to seal the inlet opening 56. When the pressure of the fluid in the compression chamber 30 drops below the pressure in the reservoir, the disc 59 unseats from the end cap 57 thus permitting fluid to flow from the reservoir through the inlet opening 56 into the compression chamber 56.

A pivot pin 73 serves to pivotally mount the lever 20 on a web 72 extending between the outlet housing 15 and the upper housing 14. A pair of lugs 74 extend from the lever 20 through slots 76 in the upper housing 14 and engage the main piston member 32 for movement thereof. Portions 83 of the lugs 74 engage ends 78 of the slots 76 to restrict travel of the lug in the direction of the arrow C. Portions 83 of the lever's lugs 74 and/or ends 78 of the housing's slots 76 act as stop means to limit the travel of the piston in the direction of arrow B. A portion 82 of the lever 20 engages the upper housing 14 when the lever 20 is at the other extreme end of its travel, see FIG. 3. Lever portion 82 and/or the upper housing 14 act as stop means to limit travel of the piston 31 in the direction of arrow A. Thus, the stroke of the piston 31 is limited in both directions and accordingly each time the lever 20 is depressed from one extreme position (FIG. 3) to the other extreme position (FIG. 4), a predetermined quantity of fluid is metered from the piston pump. Advantageously the components of the pump are dimensioned such that the predetermined quantity is 1 ml.

A hand grip 75 extends from the cap portion 9 of the housing 2 for gripping the device. Thus, with the hand grip 75 resting in the palm of the hand and the fingers round the lever 20, the lever 20 can be pivoted in the direction of the arrow C to move the piston in the direction of the arrow B. Releasing the lever 20 permits the lever to pivot in the reverse direction, thereby permitting the piston 31 to move in the direction of the arrow A under the biassing pressure of the spring 38. A guard member 77 extends from the cap portion 9 for locating the hand. A shield 79 is provided over the upper portion of the housing.

The plug 43—providing the non-return valve means in outlet housing 15—is spring biased into the outlet 39 by a spring 44. The spring 44 engages a cup member 46 which is housed in a bore 48 in the spigot cap 19. Threads 50 in the bore 48 engage corresponding threads 51 on the outlet housing 15 for securing the spigot cap 19 thereto. A pair of outlets 53 in the cup member 46 deliver fluid from the bore 42 of the outlet housing 15 into a bore 54 in the spigot cap 19. An O-ring seal 55 seals the spigot cap 19 to the outlet housing 15.

The mounting arrangement for the cannula 17 and socket 18 will now be described. A sleeve 80 is rotatably mounted on a spigot 81 of the cap 19, a bore 84 of stepped diameter extending through the sleeve 80. The smaller diameter bore portion 85 of the stepped bore 84 rotatably engages the spigot 81. A ring 86 extends round the spigot 81 of diameter slightly greater than that of the bore portion 85 to retain the sleeve 80 in position on the spigot 81, the sleeve 18 being engaged over the ring 86 with a snap fit action. The larger diameter bore portion 87 of the stepped bore 84 is provided with internal threads 89 of large pitch which engage an end plate 90 on the Luer socket 18. An end portion 91 of the spigot 81 is tapered at a Luer angle which corresponds to a corresponding Luer taper of a bore 92 in the socket 18. Such Luer lock arrangements will be known to those skilled in the art.

However, because the sleeve 80 is rotatable on the spigot 81, when the socket 18 is in sealing engagement with the tapered portion 91 of the spigot 81, the socket 18 and the cannula 17 can be rotated. This facilitates delivering of fluid into different teeth. For example, to dispense fluid into a diseased well of a lower tooth, the cannula will be oriented in the direction illustrated in FIGS. 3, 4 and 6 in which the cannula's distal portion is directed downwardly, while to dispense fluid into a diseased well in an upper tooth, the cannula, socket and sleeve will be rotated through 180° such that the cannula's distal portion is directed upwardly.

A stand 93 for supporting the device 1 when not in use is provided with a recess 94 to receive the base end of the reservoir 3. Another recess 95 forms a tray for spare or additional dispensing cannulae and sockets. These permit different people, e.g. in the same family, to be treated from the same reservoir using a different cannula for each person.

In this particular embodiment of the invention, the reservoir 3 is of plastics material and may be injection moulded or blow moulded. Indeed, as mentioned above, the device 1 may be used with a standard container in which the chlorhexidine is sold in place of the reservoir 3. The other components of the device 1, with the exception of the cannula 17, socket 18, springs 38 and 44, and the valve disc 59 are all of plastics material and most of them are injection moulded. The cannula 17, socket 18 and valve disc 59 are of stainless steel and the springs 38 and 44 are of spring steel. It will be appreciated by those skilled in the art that the components could be made of any other suitable material and, where they are of plastics material, may be produced other than by injection moulding.

In use, the reservoir 3 is filled with appropriate treatment fluid, in this case chlorhexidine, and is secured to the cap portion 9 of the housing 2. Alternatively, a full container of chlorhexidine may be screwed on to the cap portion 9. The cannula 17 and socket 18 are secured to the spigot 81 and sleeve 80. The device is then ready for use.

Initially, the compression chamber 30 is charged by pivoting the lever 20 in the direction of the arrow C. This moves the piston 31 in the direction of the arrow B thereby expelling air in the compression chamber 30 through the outlet valve plug 43 in the outlet 39. As the piston 31 moves in the direction of the arrow B, the valve disc 59 closes the inlet bore 56. On releasing the lever 20, the piston 31 moves in the direction of the arrow A under the biassing force of the spring 38. Movement of the piston in the direction of the arrow A causes the plug 43 to close the outlet 39 and the valve disc 59 to open the inlet opening 56. As the piston 31 moves in this direction, fluid is drawn into the compression chamber 30 from the reservoir 3. The device 1 is thus primed for subsequent use. For this, the cannula is inserted into the diseased pocket 23 between the tooth 24 and gum 25 (as illustrated, for a lower tooth, in FIG. 6), and the lever 20 is moved in the direction of the arrow C from the one extreme position of FIG. 3 to the other extreme position of FIG. 4, thereby to cause a predetermined metered quantity of chlorhexidine to be dispensed through the outlet 39 and on through the opening 21 in the cannula 17 into the diseased pocket 23.

It will be apparent that upon thereafter releasing the lever 20 the device 1 will be again primed and ready for use either at the same self-treatment session on another diseased pocket or at a future self-treatment session.

In certain cases, initially to clear all the air from the compression chamber 30 and the bores in the outlet housing 15, the spigot cap 19 and the cannula 17, a number of depressions of the lever 20 in the direction of the arrow C may be required.

Since the length of travel of the piston is controlled by the travel of the lever 20, each time the lever 20 is depressed from one extremity of its stroke to the other a predetermined metered quantity of fluid is dispensed (as a single "shot") from the compression chamber 30. Thus, on each use, a desired predetermined quantity of chlorhexidine is dispensed into a diseased pocket. If in any situation, the volume of the treatment fluid may need to be increased, more than one "shot", for example two or three "shots", may be readily dispensed into one or more diseased pocket. This would depend on the instructions given by the dentist, on the strength of the treatment fluid, and of course on the extent of the infection.

While a particular shape and construction of housing has been described and illustrated, any other suitable shape and construction may be used without departing from the scope of the invention. Further, it will be appreciated that the reservoir may be of any other shape or construction, and it is not necessary that the housing should be constructed to receive a container in which chlorhexidine is sold. It will of course be appreciated that the lever 20 can have a different shape and construction. Further, it will be appreciated that stop means (to restrict travel of the piston) other than stop means acting on the lever could be used. For example, it is envisaged that the piston could be arranged to move between predetermined limits formed within the piston housing, for example within the compression chamber. Such stop means could be provided by rings or projections in the compression chamber. It will also be appreciated that, although preferable, it is not essential that the inlet to the compression chamber should be provided in the piston. The inlet to the compression chamber could alternatively be provided in any other suitable location, as indeed could the outlet.

It is envisaged that other suitable arrangements for locating the dispensing means of cannula and socket onto the housing could be used. However, it is particularly advantageous that the bent cannula should be rotatably mounted on the housing so as to facilitate its use both for upper teeth and for lower teeth.

Further, in certain cases, it is envisaged that other suitable dispensing means could be used besides a cannula.

While the device according to the invention has been described for use in the treatment of periodontitis, it may be used for other dental disorders. It will also be appreciated that the device may be used for the dental treatment of humans and animals.

The invention is not limited to the exemplary embodiment hereinbefore described which may be varied in construction and detail without departing from the scope of the invention claimed.

We claim:

1. A device for dispensing a treatment fluid for the treatment of a dental disorder, the device comprising:

a housing for receiving a reservoir for storing the treatment fluid, dispensing means for dispensing treatment fluid to the area of the disorder, the said dispensing means comprising a cannula having an angled distal portion for delivery of the treatment fluid to the area of the disorder, means being provided for locating the cannula selectively in at least two positions such that the distal portion can be directed in a corresponding number of different directions, and pump means for metering and delivering a predetermined quantity of the fluid from the reservoir to the dispensing means, the said pump means comprising a piston pump having a compression chamber provided with an inlet thereto through the piston, a non-return inlet valve means in the said inlet to control fluid flow therethrough, and a tube, movable with the piston, extending from the inlet into the reservoir to draw treatment fluid therefrom, wherein stop means are provided to limit the length of the piston stroke to a predetermined length.

2. A device according to claim 1, wherein the cannula is rotable to and locatable in any position between two extreme positions that are at substantially 180° to one another.

3. A device according to claim 1, wherein the cannula is removably connectable to the housing.

4. A device according to claim 1, wherein the piston pump is actuable by a trigger-like finger-operale lever mounted pivotally on the housing, said stop means being provided by abutment of the lever (at zones distal from the lever's pivotal mounting) and the housing.

5. A device according to claim 4, wherein the said lever is pivotably movable towards and away from an elongated tubular member forming the fluid reservoir.

6. A device according to claim 5, wherein said reservoir member comprises a portion of the housing.

7. A device according to claim 5, wherein said reservoir membor is releasably connectable to the housing.

8. A device according to claim 1, wherein:

an outlet from the compression chamber of the pump is provided in a side wall of the compression chamber, the outlet communicates with a bore in a housing outlet portion that extends laterally away from an upper portion of the housing;

a non-return outlet valve means is mounted in the housing outlet portion to control fluid flow therethrough; and the housing outlet portion terminates in a tapered portion to be received in a correspondingly tapered socket of the dispensing means.

9. A device according to claim 1 wherein the cannula has an outlet in its side wall adjacent the cannula's distal end.

10. A device according to claim 1 and for the treatment of periodontitis, the reservoir containing chlorhexidine.

11. A device for dispensing a treatment fluid for the treatment of periodontal disease, the device comprising:

a housing for receiving a reservoir for storing the treatment fluid, dispensing means for dispensing treatment fluid to the area of the disorder, and pump means for metering and delivering a predetermined quantity of the fluid from the reservoir to the dispensing means, wherein the dispensing means comprises a cannula having an angled distal portion having a length and thickness for inserting between the gum tissue and tooth for delivery of the treatment fluid, means being provided for locating the cannula selectively in at least two fixed positions such that the distal portion can be directed in a corresponding number of different directions, and wherein the pump means comprises a piston pump actuable by a trigger-like finger-operable lever mounted pivotally on the housing such as to be movable towards and away from an elongated tubular member forming the said fluid reservoir, and stop means are provided by abutment of the lever and the housing, at zones distal from the lever's pivotal mounting, to limit the length of the piston stroke to a predetermined length, the said reservoir member being releasably connectable to the housing.

12. A device for dispensing a treatment fluid for the treatment of periodontal desease, the device comprising:

a housing for receiving a reservoir for storing the treatment fluid, dispensing means for dispensing treatment fluid to the area of the disorder, and pump means for metering and delivering a predetermined quantity of the fluid from the reservoir to the dispensing means, wherein the dispensing means comprises a cannula having an angled distal portion having a length and thickness for inserting between the gum tissue and tooth for delivery of the treatment fluid means being provided for rotating and locating the said cannula in any fixed position between two extreme positions that are at substantially 180° to one another such that the distal portion can be directed correspondingly in different directions, and wherein the pump means comprises a piston pump actuable by a trigger-like finger-operable lever mounted pivotally on the housing such as to be movable towards and away from an elongated tubular member forming the said fluid reservoir, and stop means are provided by abutment of the lever and the housing, at zones distal from the lever's pivotal mounting, to limit the length of the piston stroke to a predetermined length, the said reservoir member being releasably connectable to the housing.

* * * * *